(12) United States Patent
Ahmed et al.

(10) Patent No.: US 11,873,313 B1
(45) Date of Patent: Jan. 16, 2024

(54) DEVELOPMENT OF NOVEL TETRA NUCLEAR DISTORTED SQUARE ANTI-PRISM DY (III) IMINE COMPLEX FOR PHARMACEUTICAL AND INDUSTRIAL APPLICATIONS

(71) Applicant: KING FAISAL UNIVERSITY, Al-Ahsa (SA)

(72) Inventors: Hany Mohamed Ab El-Lateef Ahmed, Al-Ahsa (SA); Mai Mustafa Khalaf Ali, Al-Ahsa (SA); Ahmed M. Abu-Dief, Al-Madina Al-Mounawara (SA); Mohammed S. M. Abdelbaky, Oviedo (ES); Santiago Garcia-Granda, Oviedo (ES)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/212,426

(22) Filed: Jun. 21, 2023

(51) Int. Cl.
*C07F 17/02* (2006.01)
*C07F 15/00* (2006.01)
*C07C 6/04* (2006.01)

(52) U.S. Cl.
CPC ............... *C07F 17/02* (2013.01); *C07C 6/04* (2013.01); *C07F 15/0046* (2013.01); *C07C 2531/22* (2013.01)

(58) Field of Classification Search
None
See application file for complete search history.

(56) References Cited

PUBLICATIONS

Mandal et al. Eur. J. Inorg. Chem., 2018, 2793-2804 (Year: 2018).*
Martinić, et al., "Near-infrared emitting probes for biological imaging: Organic fluorophores, quantum dots, fluorescent proteins, lanthanide(III) complexes and nanomaterials"; Journal of Luminescence, vol. 189, Sep. 2017, pp. 19-43.
Sinicropi, et al., "Metal Complexes with Schiff Bases: Data Collection and Recent Studies on Biological Activities"; Int J Mol Sci. Dec. 2022; 23(23): 14840. Published online Nov. 27, 2022. doi: 10.3390/ijms232314840.
Sun, et al., "Series of dinuclear and tetranuclear lanthanide clusters encapsulated by salen-type and β-diketonate ligands: single-molecule magnet and fluorescence properties"; Dalton Trans., 2013, 42, 13397, issue 37.
Wang, et al., "Butterfly-shaped tetranuclear Ln4 clusters showing magnetic refrigeration and single molecule-magnet behavior", New J. Chem., 2018, DOI:10.1039/C8NJ02479K.
Biswas, et al., "Homometallic DyIII Complexes of Varying Nuclearity from 2 to 21: Synthesis, Structure, and Magnetism", Feb. 2017Chemistry—a European Journal 23(21), DOI:10.1002/chem.201700471.

* cited by examiner

*Primary Examiner* — Yun Qian
(74) *Attorney, Agent, or Firm* — Nath, Goldberg & Meyer; Richard C. Litman

(57) ABSTRACT

Provided are tetra nuclear distorted square anti-prism Dy (III) imine complexes, and their use in pharmaceutical and industrial applications. These complexes can be formed as a Schiff base-metal complex. The Schiff base-metal complex can comprise a $Dy_4L_4ES_2(H_2O)$ $H_2O$ complex, wherein L is 2-Ethoxy-6-[(2-hydroxy-phenylimino)-methyl]-phenol; and ES is deprotonated 3-ethoxysalicylaldehyde.

18 Claims, 2 Drawing Sheets
(2 of 2 Drawing Sheet(s) Filed in Color)

DEVELOPMENT OF NOVEL TETRA NUCLEAR DISTORTED SQUARE ANTI-PRISM DY (III) IMINE COMPLEX FOR PHARMACEUTICAL AND INDUSTRIAL APPLICATIONS

BACKGROUND

1. Field

The disclosure of the present patent application relates to new tetra nuclear distorted square anti-prism Dy (III) imine complexes, and their use in pharmaceutical and industrial applications.

2. Description of the Related Art

The self-assembly of polynuclear lanthanide (III) complexes has attracted much attention because of the potential use of these lanthanide complexes in the preparation of new materials and biological probes in view of their interesting magnetic and luminescent properties. On the other hand, the large and anisotropic magnetic moment for some of the lanthanide III ions makes them very appealing for the preparation of magnetic materials.

Coordination chemistry is an attractive discipline for chemists and researchers who have reached pharmacotherapeutic success in the field of remediation of severe diseases and improvements of several drugs. Schiff bases are versatile organic compounds deriving from the condensation of primary amines with carbonyl compounds; they contain an imine group (azomethine, >C=N–). In addition to their usefulness in catalysis, they show diverse biological activities including antimicrobial, antiproliferative, antimalarial, analgesic, anxiolytic, antidepressant, anti-inflammatory, antiviral, antipyretic, antibacterial, and antifungal activities. Moreover, several studies on Schiff base-metal complexes showed their use as anti-Alzheimer agents and their potential in the management of diabetes mellitus. Some Schiff base derivatives have demonstrated α-glucosidase inhibition and antiglycation activity, whereas other derivatives were synthesized and used as fluorescent sensors for the diabetic biomarker beta-hydroxybutyrate (β-HB).

Metal complexes of different metals with Schiff bases have demonstrated a myriad of activities and catalytic applications. Some exemplary metals which have been previously complexed with Schiff bases include Mo, Cu, Zr, Pd, Cu, Ni, R, Mn, Zn, and W. Several studies have been carried out on the trans-metalation of Zn-Schiff base complexes with other metal ions for various purposes, such as the detection of $Cu^{2+}$ ions in aqueous solution and the inhibition of acid-induced steel corrosion. Recent studies addressed luminescence and fluorescence taking advantage of lanthanide ($Ln^{3+}$) complexes with Schiff bases.

Not only mononuclear but also binuclear metal complexes with Schiff bases have recently attracted attention in diverse fields of research. For example, a Zn-Yb binuclear Schiff base complex, which enhanced near-infrared (NIR) luminescence, has been studies, as has a ytterbium Schiff base complex for NIR-emitting organic light emitting diode (OLED), a technology recently emerged for its use in a vast range of applications such as medical diagnostics (oximetry, drug delivery, tumor therapy, atherosclerosis treatment).

Fluorescent properties were found for mononuclear Dy(III)/heteropolynuclear Zn(II)-Dy (III) Schiff bases. Schiff base-metal complexes are frequently used as environmentally friendly catalysts. For example, Ni-Schiff base complexes have been used for green catalysis, whereas a copper (II) Schiff base complex was fixed on the surface of iron oxide nanoparticles, which was used for oxidation of olefins with $H_2O_2$ as an eco-friendly oxidant. However, the biological and pharmaceutical activities of Schiff base-metal complexes remain in need of further study, particularly for complexes beyond mononuclear and binuclear Schiff-base metal complexes.

Thus, new Schiff base-metal complexes solving the aforementioned problems are desired.

SUMMARY

The present subject matter relates to the coordination of Schiff base ligands to Dysprosium (Dy) (III) ions in tetra nuclear distorted square anti-prisms to obtain new complexes having enhanced biological activity and which are comparable with standard drugs.

In an embodiment, the present subject matter relates to a Schiff base-metal complex comprising a $Dy_4L_4ES_2(H_2O) \cdot H_2O$ complex, wherein L is 2-Ethoxy-6-[(2-hydroxyphenylimino)-methyl]-phenol; and ES is deprotonated 3-ethoxysalicylaldehyde.

In another embodiment, the present subject matter relates to a method of treating cancer in a patient, the method comprising: administering a therapeutically effective amount of the Schiff base-metal complex as described herein to a patient in need thereof.

In a further embodiment, the present subject matter relates to a method of treating a microbial infection in a patient, the method comprising: administering a therapeutically effective amount of the Schiff base-metal complex as described herein to a patient in need thereof.

In one embodiment, the present subject matter relates to a method of prompting an antioxidant response in a patient, the method comprising: administering a therapeutically effective amount of the Schiff base-metal complex as described herein to a patient in need thereof.

In still another embodiment, the present subject matter relates to a pharmaceutical composition comprising a therapeutically effective amount of the Schiff base-metal complex as described herein and a pharmaceutically acceptable carrier.

These and other features of the present subject matter will become readily apparent upon further review of the following specification.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Figure 1:
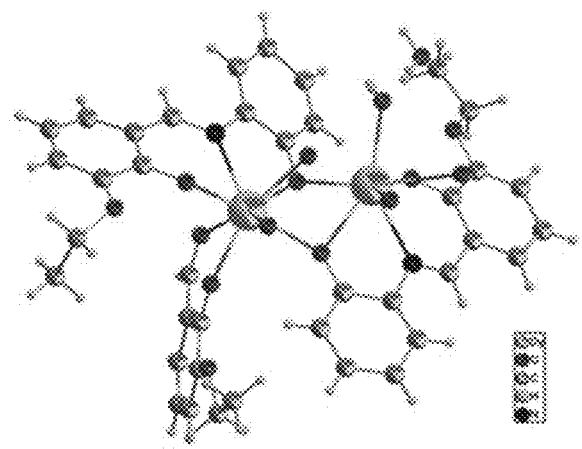
FIG. 1 shows an asymmetric view of the present $Dy_4L_4ES_2(H_2O) \cdot H_2O$ complex.
Figure 2A:
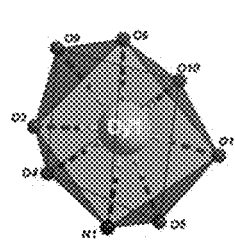
FIGS. 2A-2D show a view of the coordination environments of $Dy^{3+}$ cations (FIG. 2A, FIG. 2B), the four member ring (FIG. 2C), and the whole structure of the $Dy_4L_4ES_2(H_2O) \cdot H_2O$ complex (FIG. 2D).
Figure 2B:
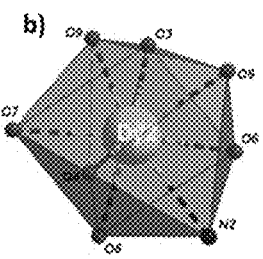
Figure 2C:
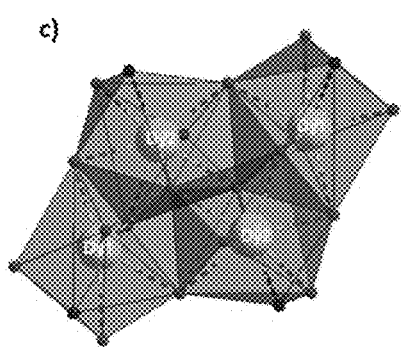
Figure 2D:
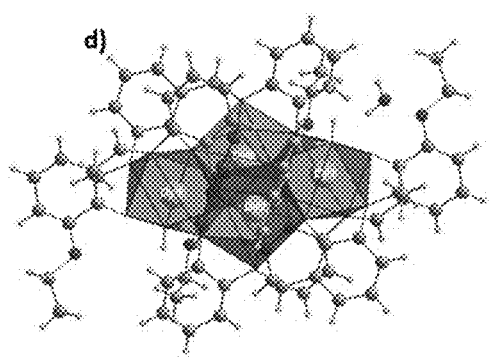

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

The present subject matter relates to the coordination of Schiff base ligands to Dysprosium (Dy) (III) ions in tetra nuclear distorted square anti-prisms to obtain new complexes having enhanced biological activity and which are comparable with standard drugs.

In an embodiment, the present subject matter relates to a Schiff base-metal complex comprising a $Dy_4L_4ES_2(H_2O) \cdot H_2O$ complex, wherein L is 2-Ethoxy-6-[(2-hydroxyphenylimino)-methyl]-phenol; and ES is deprotonated 3-ethoxysalicylaldehyde.

In one embodiment, as shown in FIG. 1, an asymmetric unit of the $Dy_4L_4ES_2(H_2O) \cdot H_2O$ complex can contain two Dy(III) cations, two Schiff base molecules (2-Ethoxy-6-[(2-hydroxy-phenylimino)-methyl]-phenol), one deprotonated 3-ethoxysalicylaldehyde, one coordinated water molecule, and one non-coordinated water molecule.

In another embodiment, $Dy^{3+}$ cations in the Schiff base-metal complex can have a distorted square antiprism structure. Further, the $Dy^{3+}$ cations can have a distance therebetween of about 3.523 Å, as shown in FIGS. 2A-2D.

Figure 3:
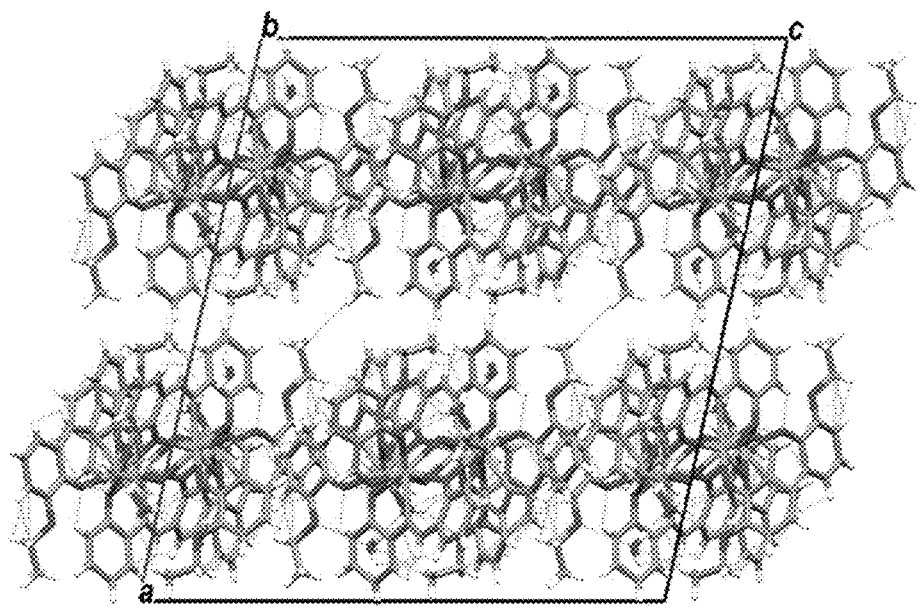
FIG. 3 shows a projection of the structure of the $Dy_4L_4ES_2(H_2O) \cdot H_2O$ complex along the αc plane.

In a further embodiment, in its crystalline state, molecules of the Schiff base-metal complex can be packed in a chained fashion, can be stabilized by O-H···O hydrogen bonds, and linked together by weak interactions of C-H···O bonds forming the 3D whole structure, as shown in FIG. 3.

In an embodiment, the Schiff base-metal complex can be configured to be used for magnetic needle manufacture of computer hard disks. In this regard, the Schiff base-metal complex can be similarly used for various other applications in the field of electronic materials.

In certain embodiments, the Schiff base-metal complex can be obtained as red crystals. Further, the Schiff base metal complex can have uniform nanoparticles.

In another embodiment, the Schiff-base metal complex is soluble in DMSO, DMF, and $CHCl_3$. Similarly, the Schiff-base metal complex is insoluble in water and diethyl ether.

In a further embodiment, the Schiff base-metal complex can crystallize in the monoclinic system with the C2/c space group. Further, the crystal structure of the Schiff base-metal can be based on an unusual four-membered ring formed by an edge and vertex shared by two crystallographically independent {DyO7N} polyhedral structures.

In still another embodiment, the present subject matter relates to a pharmaceutical composition comprising a therapeutically effective amount of the Schiff base-metal complex as described herein and a pharmaceutically acceptable carrier. In this regard, the pharmaceutically acceptable carrier can be one or more pharmaceutically acceptable carriers, excipients, or vehicles. In some embodiments, the present compositions can be used for combination therapy, where other therapeutic and/or prophylactic ingredients can be included therein.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 23rd Edition. Easton, Pa., Mack Publishing Company, 2020, the entire contents of which are incorporated by reference herein.

The present Schiff base-metal complex is typically administered at a therapeutically or pharmaceutically effective dosage, e.g., a dosage sufficient to provide treatment for, e.g., a cancer or a microbial infection. Administration of the Schiff base-metal complex or pharmaceutical compositions thereof can be by any method that delivers the Schiff base-metal complex systemically and/or locally. These methods include oral routes, parenteral routes, intraduodenal routes, and the like.

While human dosage levels have yet to be optimized for the present Schiff base-metal complex, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present Schiff base-metal complex for treatment of a disease, disorder, or condition, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present Schiff base-metal complex can also be administered in sustained or controlled release dosage forms, including depot injections, osmotic pumps, pills, transdermal (including electrotransport) patches, and the like, for the prolonged administration of the Schiff base-metal complex at a predetermined rate, preferably in unit dosage forms suitable for single administration of precise dosages.

The present Schiff base-metal complex may also be administered as compositions prepared as foods for foods or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present Schiff base-metal complex, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active Schiff base-metal complex as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active Schiff base-metal complex in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active Schiff base-metal complex contained in such parenteral compositions is highly dependent on the specific nature thereof, as well as the activity of the Schiff base-metal complex and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active Schiff base-metal complex alone or in combination with other pharmaceutically acceptable excipients can also be administered.

Formulations of the active Schiff base-metal complex may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In another embodiment, the present subject matter relates to a method of treating cancer in a patient, the method comprising: administering a therapeutically effective amount of the Schiff base-metal complex as described herein to a patient in need thereof. In certain embodiments, the cancer can be colon cancer or breast cancer. Other specific cancers are considered to be treatable according to the methods described herein.

In a further embodiment, the present subject matter relates to a method of treating a microbial infection in a patient, the method comprising: administering a therapeutically effective amount of the Schiff base-metal complex as described herein to a patient in need thereof.

In this regard, the microbial infection can be a bacterial infection or a fungal infection. In certain embodiments, the bacterial infection can be caused by E. coli.

In one embodiment, the present subject matter relates to a method of prompting an antioxidant response in a patient, the method comprising: administering a therapeutically effective amount of the Schiff base-metal complex as described herein to a patient in need thereof.

The present Schiff base-metal complexes can also be used in other treatment methods. By way of non-limiting example, the present Schiff base-metal complexes can be used for their antimicrobial, antiproliferative, antimalarial, analgesic, anxiolytic, antidepressant, anti-inflammatory, antiviral, antipyretic, antibacterial, and antifungal properties. Moreover, the present Schiff base-metal complexes can be used as anti-Alzheimer agents and in the management of diabetes mellitus. Similarly, the present Schiff base-metal complexes can be used as fluorescent sensors, including by way of non-limiting example as a fluorescent sensor for the diabetic biomarker beta-hydroxybutyrate (β-HB).

The present teachings are illustrated by the following examples.

EXAMPLES

Example 1

Preparation of the Schiff base-metal complex

NaOH (0.32 g, 8 mmol in 10 ml water) was added to a solution of ligand (2-Ethoxy-6-[(2-hydroxy-phenylimino)-methyl]-phenol) (1.028 g, 4 mmol) in ethanol and the resulting solution was stirred for 30 min. Then, 0.366 g $EuCl_3 \cdot 6H_2O$ (1 mmol) dissolved in 25 mL of water were added slowly to the initial solution. The resulting solution was stirred for 2 hours. The resulting deep red precipitate was filtered, washed with $H_2O$, and dried with $Et_2O$. Red crystals were obtained by layering $CHCl_3$ with $Et_2O$.

Figure 4:
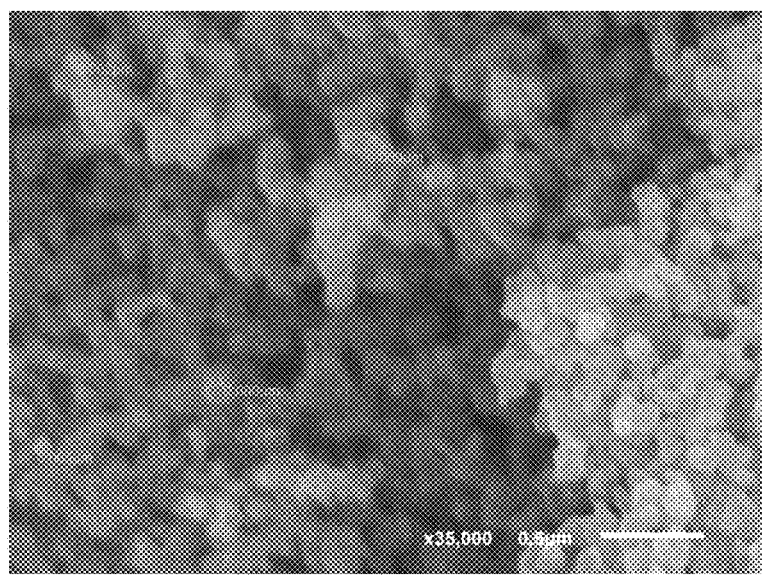
FIG. 4 shows a SEM image for the prepared $Dy_4L_4ES_2(H_2O) \cdot H_2O$ complex.

FIG. 4 shows an SEM image of the obtained complex with high crystallinity and uniform nanoparticles.

Example 2

Anti-microbial activity

The prepared novel complex showed potent antibacterial activity against E-coli bacteria with an inhibition zone of 35 mm and an MIC of 1.3 µg/ml compared with the standard drug Ofloxacin (30 mm and MIC 2.25 µg/ml).

Example 3

Anti-cancer activity

The prepared novel complex showed anticancer activity with an $IC_{50}$ of 4.3 µg/ml against a colon cancer cell line compared with the vinblastine standard drug ($IC_{50}$=4.7 µg/ml).

Example 4

Anti-oxidant activity

The prepared novel complex showed Antioxidant activity with an $IC_{50}$ of 9.7 µg/ml against the breast cancer cell line compared with the 1-ascorbic acid standard antioxidant (IC50=55.2 µg/ml).

It is to be understood that the Schiff base-metal complex is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A Schiff base-metal complex comprising a $Dy_4L_4ES_2(H_2O) \cdot H_2O$ complex, wherein:
   L is 2-Ethoxy-6-[(2-hydroxy-phenylimino)-methyl]-phenol; and
   ES is deprotonated 3-ethoxysalicylaldehyde.

2. The Schiff base-metal complex of claim 1, wherein an asymmetric unit of the $Dy_4L_4ES_2(H_2O) \cdot H_2O$ complex contains two Dy(III) cations, two Schiff base molecules (2-Ethoxy-6-[(2-hydroxy-phenylimino)-methyl]-phenol), one deprotonated 3-ethoxysalicylaldehyde, one coordinated water molecule, and one non-coordinated water molecule.

3. The Schiff base-metal complex of claim 1, wherein $Dy^{3+}$ cations in the Schiff base-metal complex have a distorted square antiprism structure.

4. The Schiff base-metal complex of claim 3, wherein a distance between the $Dy^{3+}$ cations is about 3.523 Å.

5. The Schiff base-metal complex of claim 1, wherein, in its crystalline state, molecules of the Schiff base-metal complex are packed in a chained fashion, are stabilized by O-H···O hydrogen bonds and linked together by weak interactions of C-H···O bonds.

6. The Schiff base-metal complex of claim 1, configured to be used for magnetic needle manufacture of computer hard disks.

7. The Schiff base-metal complex of claim 1, obtained as red crystals.

8. The Schiff base-metal complex of claim 1, wherein the Schiff base-metal complex is soluble in DMSO, DMF, and $CHCl_3$.

9. The Schiff base-metal complex of claim 1, wherein the Schiff base-metal complex is insoluble in water and diethyl ether.

10. The Schiff base-metal complex of claim 1, having uniform nanoparticles.

11. A method of treating cancer in a patient, the method comprising:
    administering a therapeutically effective amount of the Schiff base-metal complex of claim 1 to a patient in need thereof.

12. The method of claim 11, wherein the cancer is colon cancer or breast cancer.

13. A method of treating a microbial infection in a patient, the method comprising:
    administering a therapeutically effective amount of the Schiff base-metal complex of claim 1 to a patient in need thereof.

14. The method of claim 13, wherein the microbial infection is a bacterial infection.

15. The method of claim 14, wherein the bacterial infection is caused by E. coli.

16. The method of claim 13, wherein the microbial infection is a fungal infection.

17. A method of prompting an antioxidant response in a patient, the method comprising:
    administering a therapeutically effective amount of the Schiff base-metal complex of claim 1 to a patient in need thereof.

18. A pharmaceutical composition, comprising a therapeutically effective amount of the Schiff-base metal complex of claim 1 and a pharmaceutically acceptable carrier.

* * * * *